United States Patent [19]

van Beek

[11] Patent Number: 5,646,083
[45] Date of Patent: Jul. 8, 1997

[54] PROCESS FOR THE PREPARATION OF A BRIDGED METALLOCENE COMPOUND AS WELL AS A CATALYST COMPONENT AND A PROCESS FOR THE POLYMERIZATION OF OLEFINS

[75] Inventor: Johannus A.M. van Beek, Brunssum, Netherlands

[73] Assignee: DSM N.V., Netherlands

[21] Appl. No.: 202,738

[22] Filed: Feb. 28, 1994

Related U.S. Application Data

[63] Continuation of Ser. No. 940,287, Sep. 3, 1992, abandoned.

[30] Foreign Application Priority Data

Sep. 6, 1991 [NL] Netherlands ............... 9101502

[51] Int. Cl.$^6$ .......................................... C08F 4/42
[52] U.S. Cl. ................ 502/104; 502/117; 502/126; 502/155; 502/156; 526/160; 556/11; 556/12; 556/53
[58] Field of Search ..................... 502/104, 117, 502/126, 155, 156; 556/11, 12, 53; 526/160

[56] References Cited

U.S. PATENT DOCUMENTS

| | | | |
|---|---|---|---|
| 4,892,851 | 1/1990 | Ewen et al. | 502/104 |
| 5,103,030 | 4/1992 | Rohrmann et al. | 556/12 |
| 5,117,020 | 5/1992 | Razavi | 556/43 |
| 5,132,381 | 7/1992 | Winter et al. | 526/160 |
| 5,158,920 | 10/1992 | Razavi | 502/152 |

FOREIGN PATENT DOCUMENTS

| | | |
|---|---|---|
| 320762 | 6/1989 | European Pat. Off. . |
| 0427696 | 9/1990 | European Pat. Off. . |
| 420436 | 4/1991 | European Pat. Off. . |
| 427697 | 5/1991 | European Pat. Off. . |
| 3193797 | 8/1991 | Japan . |
| WO9106551 | 5/1991 | WIPO . |

*Primary Examiner*—David W. Wu
*Attorney, Agent, or Firm*—Cushman Darby & Cushman IP Group of Pillsbury Madison & Sutro, LLP

[57] ABSTRACT

The invention relates to a process for the preparation of a bridged metallocene compound in which:

(I) a bridged double ligand, reacting with a proton acceptor, is converted into a bridged double anion (II) the double anion is converted into the bridged metallocene compound through reaction with a compound of a group 4b, 5b or 6b metal from the Periodic System of Elements.

reaction (II) being carried out in a liquid dispersant which a) comprises one or more weak Lewis bases, the conjugated acid of which has a dissociation constant $pK_a$ for which the following holds:

$pK_a \leq -2.5$, b) contains at most 1 mole equivalent, relevant to the metal compound, of strong Lewis base, the conjugated acid of which has a $pK_a$ that is higher than −2.5.

The invention further relates to a catalyst component for the polymerization of olefins and a process for the polymerization of olefins and a polyolefin.

15 Claims, No Drawings

PROCESS FOR THE PREPARATION OF A BRIDGED METALLOCENE COMPOUND AS WELL AS A CATALYST COMPONENT AND A PROCESS FOR THE POLYMERIZATION OF OLEFINS

This is a continuation of application Ser. No. 07/940,287, filed Sep. 3, 1992, and now abandoned.

The invention relates to a process for the preparation of a bridged metallocene compound in which:

(I) a bridged double ligand, reacting with a proton acceptor, is converted into a bridged double anion (II) the double anion is converted into the bridged metallocene compound through a reaction with a compound of a group 4b, 5b or 6b metal from the Periodic System of Elements.

The Periodic System of Elements is understood to be the table as shown inside the cover of the Handbook of Chemistry and Physics, 58th Edition, CRC Press, 1977–1978.

The invention further relates to a catalyst component for the polymerization of olefins and a process for the polymerization of olefins and a polyolefin.

A process for the preparation of a bridged metallocene compound is known from EP-A-0351392, which discloses the preparation of a bridged dicyclopentadienyl metallocene compound of the general formula:

$$R''(CpR_n)(CpR'_m)MeQ_k \qquad (1)$$

in which the symbols have the following meanings:

Cp cyclopentadienyl ring or substituted cyclopentadienyl ring $R_n$ hydrocarbon radical with 1–20 C atoms $R'_m$ hydrocarbon radical with 1–20 C atoms R'' structural bridge between the Cp rings Me group 4b, 5b or 6b metal from the Periodic System of Elements Q hydrocarbon radical with 1–20 C atoms or halogen k, m and n are integers, with $k \leq 3$, $0 \leq n \leq 4$ and $1 \leq m \leq 4$.

The metallocene compound isopropyl (9-fluorenyl)(1-cyclopentadienyl) zirconium dichloride is obtained in a yield of 42% in reaction (II). The method is described on page 6 of EP-A-0351392 (method B), where 5.5 g of metallocene compound, with a molecular weight of 519.5 g/mol, is prepared from 0.025 mol of bridged double anion. This yield is on the high side of the yields customarily found for the preparation of bridged metallocene compounds, but still is low and therefore disadvantageous for the process economy. Moreover, the metallocene compounds prepared according to EP-A-0351392 have a low stability. They decompose easily as a solid or dissolved in a solvent and as a result their activity as a catalyst component decreases. In view of this, the metallocene compounds according to EP-A-0351392 are purified in an additional step or stored in dry, oxygen-free argon.

The object of the invention is to provide a simple process for the preparation of a bridged metallocene compound with improved yield.

According to the invention this is accomplished in that reaction (II) is carried out in a liquid dispersant which:

a) comprises one or more weak Lewis bases, the conjugated acid of which has a dissociation constant $pK_a$ for which the following holds:

$pK_a \leq -2.5$, b) contains at most 1 mole equivalent, relevant to the metal compound, of strong Lewis base, the conjugated acid of which has a $pK_a$ that is higher than $-2.5$. The $pK_a$ values are based on D. D. Perrin: Dissociation Constants of Organic Bases in Aqueous Solution, International Union of Pure and Applied Chemistry, Butterworths, London 1965. The values were determined in an aqueous $H_2SO_4$ solution.

Surprisingly, according to the invention high yields are achieved in the preparation of the metallocene compounds and the resulting compounds prove to have a much higher stability than the known metallocene compounds.

There is a great deal of interest in metallocene compounds for use as a catalyst component in the polymerization of olefins. The metallocene compounds are generally used with linear or cyclic alumoxanes as a cocatalyst for homo- or copolymerization of olefins, for instance for the preparation of polyethylene, polypropylene and ethylene-propylene-diene-monomer-(EPDM) rubbers. The catalysts exhibit a high activity and render it possible to produce polymers with a high degree of uniformity, for instance with a narrow molecular weight distribution. For this reason there have been a great many publications in the field of the preparation of the metallocene catalysts and their application in polymerization reactions. Examples are US-A-4522982, EP-A-0284707, EP-A-0284708, EP-A-310734, EP-A-0310738, DE-A-3640924, EP-A-0302424, EP-A-0069951, DE-A3443087 and DE-A-3640948.

The advantage of bridged metallocene compounds as described in EP-A-0351392 is that they have a rigid structure. When they are used as catalyst component, this structure makes it possible to prepare polymers having a certain stereo configuration, for instance almost completely isotactic or syndiotactic polypropylene.

The synthesis of bridged metallocene compounds is disclosed inter alia in EP-A-0316155, WO-A-90/07526 and JP-A-90/173104. In the examples of these publications reaction (II) takes place in the presence of tetrahydrofuran, which is a strong Lewis base, the conjugated acid having a $pK_a$ of $-2.08$. When tetrahydrofuran is used as solvent the yields are low.

EP-A-0320762 does disclose the use of a weak Lewis base as liquid dispersant; however, more than 1 mole equivalent of strong Lewis base is present since use is made of zirconium tetrachloride complexed with 2 mole equivalents of tetrahydrofuran. The yield of the dimethylsilyl bis(1-indenyl) zirconium dichloride compound is only 22%.

In addition, EP-A-0351392 discloses the use of dichloromethane, but this is a non-coordinating solvent. There is no indication of the existence of the conjugated acid of dichloromethane. The $pK_a$ of the conjugated acid of dichloromethane is mentioned neither in Perrin, nor in Beilstein's 'Handbuch der organischen Chemie', 4th ed., Springer, Berlin (1956). Dichloro methane cannot be regarded as a weak base according to the invention. Moreover, the dichloro methane may react with the organolithium compound. The yield is 42% at most.

According to the invention yields higher than 60% are obtained.

A disadvantage of the bridged metallocene compounds is that synthesis using the known techniques is difficult and the synthesis yields are low. Furthermore, the bridged metallocene compounds obtained as reaction product have a low stability.

Polymerization of olefins with metallocene compounds is generally effected in the presence of an aromatic dispersant; in all examples of the above-mentioned literature toluene is used as solvent. However, in view of the cost price and for safety considerations it will generally not be considered desirable to use such dispersants in technical-scale production. For technical-scale polymerizations the cheaper aliphatic hydrocarbons, or mixtures thereof, as marketed by the petrochemical industry, are preferably used. Thus, fractionated hexane or gasoline, for instance, is a customary reaction medium in olefin polymerizations. Although many of the above-mentioned patent publications mention the possibility of polymerization in gasoline, in the examples the polymerization is effected only in toluene.

The process according to the invention is suitable for the preparation of bridged metallocene compounds of the following formula:

in which the symbols have the following meanings:

$CpR_n$ cyclopentadienyl, indenyl or fluorenyl group, whether or not substituted with one or more alkyl, phosphine, amine, alkyl ether or aryl ether groups $CpR'_m$ cyclopentadienyl, indenyl or fluorenyl group, whether or not substituted with one or more alkyl, phosphine, amine, alkyl ether or aryl ether groups R" structural bridge between the Cp rings Me group 4b, 5b or 6b metal from the Periodic System of Elements Q alkyl-, aryl-, aryl alkyl-, alkyl aryl-, amide-, alkoxy-, halogenide-, sulphide-, hydride- or phosphorus-containing group; the groups Q may be the same or different.

m, n and p are integers, with $0 \leq n \leq 4$, $0 \leq m \leq 4$ and $1 \leq p \leq 4$.

Examples of the bridged metallocene compounds according to the invention are:

dimethylsilyl bis(1-indenyl) zirconium dibromide
dimethylsilyl bis(1-indenyl) zirconium diethyl
dimethylsilyl bis(1-indenyl) zirconium dimethoxide
dimethylsilyl bis(1-indenyl) zirconium dihydride
dimethylsilyl bis(1-indenyl) zirconium chloride bromide
dimethylsilyl bis(1-indenyl) zirconium chloride methoxide
dimethylsilyl bis(1-indenyl) zirconium chloride methyl
dimethylsilyl bis(1-indenyl) zirconium chloride hydride
dimethylsilyl (9-fluorenyl)(1-cyclopentadienyl) zirconium dichloride
dimethylsilyl (9-fluorenyl)(1-cyclopentadienyl) zirconium dimethyl
dimethylsilyl (9-fluorenyl)(1-cyclopentadienyl) zirconium diethoxide
dimethylsilyl bis(9-fluorenyl) zirconium dichloride
dimethylsilyl bis(9-fluorenyl) zirconium dimethyl
dimethylsilyl bis(9-fluorenyl) zirconium diethoxide
dimethylsilyl bis(1-cyclopentadienyl) zirconium dichloride
dimethylsilyl bis(1-cyclopentadienyl) zirconium dimethyl
dimethylsilyl bis(1-cyclopentadienyl) zirconium diethoxide
dimethylsilyl bis(1-indenyl) zirconium dichloride
dimethylsilyl bis(1-indenyl) zirconium dimethyl
dimethylsilyl bis(1-indenyl) zirconium diethoxide
dimethylsilyl (1-indenyl)(1-cyclopentadienyl) zirconium dichloride
dimethylsilyl (1-indenyl)(1-cyclopentadienyl) zirconium dimethyl
dimethylsilyl (1-indenyl)(1-cyclopentadienyl) zirconium diethoxide
dimethylsilyl (1-indenyl)(9-fluorenyl) zirconium dichloride
dimethylsilyl (1-indenyl)(9-fluorenyl) zirconium dimethyl
dimethylsilyl (1-indenyl)(9-fluorenyl)zirconium diethoxide
dimethylsilyl (9-fluorenyl)(1-cyclopentadienyl) hafnium dichloride
dimethylsilyl (9-fluorenyl)(1-cyclopentadienyl) hafnium dimethyl
dimethylsilyl (9-fluorenyl)(1-cyclopentadienyl) hafnium diethoxide
dimethylsilyl bis(9-fluorenyl) hafnium dichloride
dimethylsilyl bis(9-fluorenyl) hafnium dimethyl
dimethylsilyl bis(9-fluorenyl) hafnium diethoxide
dimethylsilyl bis(1-cyclopentadienyl) hafnium dichloride
dimethylsilyl bis(1-cyclopentadienyl) hafnium dimethyl
dimethylsilyl bis(1-cyclopentadienyl) hafnium diethoxide
dimethylsilyl bis(1-indenyl) hafnium dichloride
dimethylsilyl bis(1-indenyl) hafnium dimethyl
dimethylsilyl bis(1-indenyl) hafnium diethoxide
dimethylsilyl(1-indenyl)(1-cyclopentadienyl) hafnium dichloride
dimethylsilyl (1-indenyl)(1-cyclopentadienyl) hafnium dimethyl
dimethylsilyl (1-indenyl)(1-cyclopentadienyl) hafnium diethoxide
dimethylsilyl (1-indenyl)(9-fluorenyl) hafnium dichloride
dimethylsilyl (1-indenyl)(9-fluorenyl) hafnium dimethyl
dimethylsilyl (1-indenyl)(9-fluorenyl) hafnium diethoxide
2.2-propyl bis(1-indenyl) zirconium dibromide
2.2-propyl bis(1-indenyl) zirconium diethyl
2.2-propyl bis(1-indenyl) zirconium dimethoxide
2.2-propyl bis(1-indenyl) zirconium dihydride
2.2-propyl bis(1-indenyl) zirconium chloride bromide
2.2-propyl bis(1-indenyl) zirconium chloride methoxide
2.2-propyl bis(1-indenyl) zirconium chloride methyl
2.2-propyl bis(1-indenyl) zirconium chloride hydride
2.2-propyl bis(trimethyl cyclopentadienyl) zirconium dichloride
2.2-propyl bis(5-dimethylamino-1-indenyl) zirconium dichloride
2.2-propyl bis(6-dipropylamino-1-indenyl) zirconium dichloride
2.2-propyl bis(4,7-bis(dimethylamino)-1-indenyl) zirconium dichloride
2.2-propyl bis(5-diphenylphosphino-1-indenyl) zirconium dichloride
2.2-propyl (1-dimethylamino-9-fluorenyl)(1-cyclopentadienyl) zirconium dichloride
2.2-propyl (4-butylthio-9-fluorenyl)(1-cyclopentadienyl) zirconium dichloride
2.2-propyl bis(4,5,6,7-tetrahydro-1-indenyl) zirconium dichloride
2.2-propyl bis(4-methyl-1-indenyl) zirconium dichloride 2,2-propyl bis(5-methyl-1-indenyl) zirconium dichloride
2,2-propyl bis(6-methyl-1-indenyl) zirconium dichloride
2,2-propyl bis(7-methyl-1-indenyl) zirconium dichloride
2,2-propyl bis(5-methoxy-1-indenyl) zirconium dichloride
2,2-propyl bis(4,7-dimethoxy-1-indenyl) zirconium dichloride
2,2-propyl bis(2,3-dimethyl-1-indenyl) zirconium dichloride
2,2-propyl bis(4,7-dimethyl-1-indenyl) zirconium dichloride
2,2-propyl (9-fluorenyl)(1-cyclopentadienyl) zirconium dichloride
2,2-propyl (9-fluorenyl)(1-cyclopentadienyl) zirconium dimethyl
2,2-propyl (9-fluorenyl)(1-cyclopentadienyl) zirconium diethoxide
2,2-propyl bis(9-fluorenyl) zirconium dichloride
2,2-propyl bis(9-fluorenyl) zirconium dimethyl
2,2-propyl bis(9-fluorenyl) zirconium diethoxide
2,2-propyl bis(1-cyclopentadienyl) zirconium dichloride
2,2-propyl bis(1-cyclopentadienyl) zirconium dimethyl
2,2-propyl bis(1-cyclopentadienyl) zirconium diethoxide
2,2-propyl bis(1-indenyl) zirconium dichloride
2,2-propyl bis(1-indenyl) zirconium dimethyl
2,2-propyl bis(1-indenyl) zirconium diethoxide
2,2-propyl (1-indenyl)(1-cyclopentadienyl) zirconium dichloride
2,2-propyl (1-indenyl)(1-cyclopentadienyl) zirconium dimethyl
2,2-propyl (1-indenyl)(1-cyclopentadienyl) zirconium diethoxide
2,2-propyl (1-indenyl)(9-fluorenyl) zirconium dichloride
2,2-propyl (1-indenyl)(9-fluorenyl) zirconium dimethyl
2,2-propyl (1-indenyl)(9-fluorenyl) zirconium diethoxide
2,2-propyl (9-fluorenyl)(1-cyclopentadienyl) hafnium dichloride
2,2-propyl (9-fluorenyl)(1-cyclopentadienyl) hafnium dimethyl
2,2-propyl (9-fluorenyl)(1-cyclopentadienyl) hafnium diethoxide
2,2-propyl bis(9-fluorenyl) hafnium dichloride
2,2-propyl bis(9-fluorenyl) hafnium dimethyl
2,2-propyl bis(9-fluorenyl) hafnium diethoxide
2,2-propyl bis(1-cyclopentadienyl) hafnium dichloride
2,2-propyl bis(1-cyclopentadienyl) hafnium dimethyl
2,2-propyl bis(1-cyclopentadienyl) hafnium diethoxide
2,2-propyl bis(1-indenyl) hafnium dichloride
2,2-propyl bis(1-indenyl) hafnium dimethyl
2,2-propyl bis(1-indenyl) hafnium diethoxide
2,2-propyl (1-indenyl)(1-cyclopentadienyl) hafnium dichloride
2,2-propyl (1-indenyl)(1-cyclopentadienyl) hafnium dimethyl
2,2-propyl (1-indenyl)(1-cyclopentadienyl) hafnium diethoxide
2,2-propyl (1-indenyl)(9-fluorenyl) hafnium dichloride
2,2-propyl (1-indenyl)(9-fluorenyl) hafnium dimethyl
2,2-propyl (1-indenyl)(9-fluorenyl) hafnium diethoxide diphenyl methyl bis(1-indenyl) zirconium dibromide
diphenyl methyl bis(1-indenyl) zirconium diethyl
diphenyl methyl bis(1-indenyl) zirconium dimethoxide
diphenyl methyl bis(1-indenyl) zirconium dihydride
diphenyl methyl bis(1-indenyl) zirconium chloride bromide
diphenyl methyl bis(1-indenyl) zirconium chloride methoxide
diphenyl methyl bis(1-indenyl) zirconium chloride methyl
diphenyl methyl bis(1-indenyl) zirconium chloride hydride
diphenyl methyl(9-fluorenyl)(1-cyclopentadienyl) zirconium dichloride
diphenyl methyl(9-fluorenyl)(1-cyclopentadienyl) zirconium dimethyl
diphenyl methyl(9-fluorenyl)(1-cyclopentadienyl) zirconium diethoxide
diphenyl methyl bis(9-fluorenyl) zirconium dichloride
diphenyl methyl bis(9-fluorenyl) zirconium dimethyl
diphenyl methyl bis(9-fluorenyl) zirconium diethoxide
diphenyl methyl bis(1-cyclopentadienyl) zirconium dichloride
diphenyl methyl bis(1-cyclopentadienyl) zirconium dimethyl
diphenyl methyl bis(1-cyclopentadienyl) zirconium diethoxide
diphenyl methyl bis(1-indenyl) zirconium dichloride
diphenyl methyl bis(1-indenyl) zirconium dimethyl
diphenyl methyl bis(1-indenyl) zirconium diethoxide
diphenyl methyl (1-indenyl)(1-cyclopentadienyl) zirconium dichloride
diphenyl methyl (1-indenyl)(1-cyclopentadienyl) zirconium dimethyl
diphenyl methyl (1-indenyl)(1-cyclopentadienyl) zirconium diethoxide
diphenyl methyl (1-indenyl)(9-fluorenyl) zirconium dichloride
diphenyl methyl (1-indenyl)(9-fluorenyl) zirconium dimethyl
diphenyl methyl (1-indenyl)(9-fluorenyl) zirconium diethoxide
diphenyl methyl (9-fluorenyl)(1-cyclopentadienyl) hafnium dichloride
diphenyl methyl (9-fluorenyl)(1-cyclopentadienyl) hafnium dimethyl
diphenyl methyl (9-fluorenyl)(1-cyclopentadienyl) hafnium diethoxide
diphenyl methyl bis(9-fluorenyl) hafnium dichloride
diphenyl methyl bis(9-fluorenyl) hafnium dimethyl
diphenyl methyl bis(9-fluorenyl) hafnium diethoxide
diphenyl methyl bis(1-cyclopentadienyl) hafnium dichloride
diphenyl methyl bis(1-cyclopentadienyl) hafnium dimethyl
diphenyl methyl bis(1-cyclopentadienyl) hafnium diethoxide
diphenyl methyl bis(1-indenyl) hafnium dichloride
diphenyl methyl bis(1-indenyl) hafnium dimethyl
diphenyl methyl bis(1-indenyl) hafnium diethoxide diphenyl methyl (1-indenyl)(1-cyclopentadienyl) hafnium dichloride diphenyl methyl (1-indenyl)(1-cyclopentadienyl) hafnium dimethyl diphenyl methyl (1-indenyl)(1-cyclopentadienyl) hafnium diethoxide diphenyl methyl (1-indenyl)(9-fluorenyl) hafnium dichloride diphenyl methyl (1-indenyl)(9-fluorenyl) hafnium dimethyl diphenyl methyl (1-indenyl)(9-fluorenyl) hafnium diethoxide diphenylsilyl bis(1-indenyl) zirconium dibromide
diphenylsilyl bis(1-indenyl) zirconium diethyl
diphenylsilyl bis(1-indenyl) zirconium dimethoxide
diphenylsilyl bis(1-indenyl) zirconium dihydride
diphenylsilyl bis(1-indenyl) zirconium chloride bromide
diphenylsilyl bis(1-indenyl) zirconium chloride methoxide
diphenylsilyl bis(1-indenyl) zirconium chloride methyl
diphenylsilyl bis(1-indenyl) zirconium chloride hydride
diphenylsilyl (9-fluorenyl)(1-cyclopentadienyl) zirconium dichloride
diphenylsilyl (9-fluorenyl)(1-cyclopentadienyl) zirconium dimethyl
diphenylsilyl (9-fluorenyl)(1-cyclopentadienyl) zirconium diethoxide
diphenylsilyl bis(9-fluorenyl) zirconium dichloride
diphenylsilyl bis(9-fluorenyl) zirconium dimethyl
diphenylsilyl bis(9-fluorenyl) zirconium diethoxide
diphenylsilyl bis(1-cyclopentadienyl) zirconium dichloride
diphenylsilyl bis(1-cyclopentadienyl) zirconium dimethyl
diphenylsilyl bis(1-cyclopentadienyl) zirconium diethoxide
diphenylsilyl bis(1-indenyl) zirconium dichloride
diphenylsilyl bis(1-indenyl) zirconium dimethyl
diphenylsilyl bis(1-indenyl) zirconium diethoxide
diphenylsilyl (1-indenyl)(1-cyclopentadienyl) zirconium dichloride
diphenylsilyl (1-indenyl)(1-cyclopentadienyl) zirconium dimethyl
diphenylsilyl (1-indenyl)(1-cyclopentadienyl) zirconium diethoxide
diphenylsilyl (1-indenyl)(9-fluorenyl) zirconium dichloride
diphenylsilyl (1-indenyl)(9-fluorenyl) zirconium dimethyl
diphenylsilyl (1-indenyl)(9-fluorenyl) zirconium diethoxide
diphenylsilyl (9-fluorenyl)(1-cyclopentadienyl) hafnium dichloride
diphenylsilyl (9-fluorenyl)(1-cyclopentadienyl) hafnium dimethyl
diphenylsilyl (9- fluorenyl)(1-cyclopentadienyl) hafnium diethoxide
diphenylsilyl bis(9-fluorenyl) hafnium dichloride
diphenylsilyl bis(9-fluorenyl) hafnium dimethyl
diphenylsilyl bis(9-fluorenyl) hafnium diethoxide
diphenylsilyl bis(1-cyclopentadienyl) hafnium dichloride
diphenylsilyl bis(1-cyclopentadienyl) hafnium dimethyl
diphenylsilyl bis(1-cyclopentadienyl) hafnium diethoxide
diphenylsilyl bis(1-indenyl) hafnium dichloride
diphenylsilyl bis(1-indenyl) hafnium dimethyl
diphenylsilyl bis(1-indenyl) hafnium diethoxide
diphenylsilyl (1-indenyl)(1-cyclopentadienyl) hafnium dichloride
diphenylsilyl (1-indenyl)(1-cyclopentadienyl) hafnium dimethyl
diphenylsilyl (1-indenyl)(1-cyclopentadienyl) hafnium diethoxide
diphenylsilyl (1-indenyl)(9-fluorenyl) hafnium dichloride
diphenylsilyl (1-indenyl)(9-fluorenyl) hafnium dimethyl
diphenylsilyl (1-indenyl)(9-fluorenyl) hafnium diethoxide
ethylene bis(1-indenyl) zirconium dibromide
ethylene bis(1-indenyl) zirconium diethyl
ethylene bis(1-indenyl) zirconium dimethoxide
ethylene bis(1-indenyl) zirconium dihydride
ethylene bis(1-indenyl) zirconium chloride bromide
ethylene bis(1-indenyl) zirconium chloride methoxide
ethylene bis(1-indenyl) zirconium chloride methyl
ethylene bis(1-indenyl) zirconium chloride hydride
ethylene bis(trimethyl cyclopentadienyl) zirconium dichloride
ethylene bis(5-dimethylamino-1-indenyl) zirconium dichloride
ethylene bis(6-dipropylamino-1-indenyl) zirconium dichloride
ethylene bis(4,7-bis(dimethylamino)-1-indenyl) zirconium dichloride
ethylene bis(5-diphenylphosphino-1-indenyl) zirconium dichloride
ethylene (1-dimethylamino-9-fluorenyl)(1-cyclopentadienyl) zirconium dichloride
ethylene (4-butylthio-9-fluorenyl)(1-cyclopentadienyl) zirconium dichloride
ethylene bis(4,5,6,7-tetrahydro-1-indenyl) zirconium dichloride
ethylene bis(4-methyl-1-indenyl) zirconium dichloride
ethylene bis(5-methyl-1-indenyl) zirconium dichloride
ethylene bis(6-methyl-1-indenyl) zirconium dichloride
ethylene bis(7-methyl-1-indenyl) zirconium dichloride
ethylene bis(5-methoxy-1-indenyl) zirconium dichloride
ethylene bis(4,7-methoxy-1-indenyl) zirconium dichloride
ethylene bis(2,3-dimethyl-1-indenyl) zirconium dichloride
ethylene bis(4,7-dimethyl-1-indenyl) zirconium dichloride
ethylene (9-fluorenyl)(1-cyclopentadienyl) zirconium dichloride
ethylene (9-fluorenyl)(1-cyclopentadienyl) zirconium dimethyl
ethylene (9-fluorenyl)(1-cyclopentadienyl) zirconium diethoxide
ethylene bis(9-fluorenyl) zirconium dichloride
ethylene bis(9-fluorenyl) zirconium dimethyl
ethylene bis(9-fluorenyl) zirconium diethoxide
ethylene bis(1-cyclopentadienyl) zirconium dichloride ethylene bis(1-cyclopentadienyl) zirconium dimethyl
ethylene bis(1-cyclopentadienyl) zirconium diethoxide
ethylene bis(1-indenyl) zirconium dichloride
ethylene bis(1-indenyl) zirconium dimethyl
ethylene bis(1-indenyl) zirconium diethoxide
ethylene (1-indenyl)(1-cyclopentadienyl) zirconium dichloride
ethylene (1-indenyl)(1-cyclopentadienyl) zirconium dimethyl
ethylene (1-indenyl)(1-cyclopentadienyl) zirconium diethoxide
ethylene (1-indenyl)(9-fluorenyl) zirconium dichloride
ethylene (1-indenyl)(9-fluorenyl) zirconium dimethyl
ethylene (1-indenyl)(9-fluorenyl) zirconium diethoxide
ethylene (9-fluorenyl)(1-cyclopentadienyl) hafnium dichloride
ethylene (9-fluorenyl)(1-cyclopentadienyl) hafnium dimethyl
ethylene (9-fluorenyl)(1-cyclopentadienyl) hafnium diethoxide
ethylene bis(9-fluorenyl) hafnium dichloride
ethylene bis(9-fluorenyl) hafnium dimethyl
ethylene bis(9-fluorenyl) hafnium diethoxide
ethylene bis(1-cyclopentadienyl) hafnium dichloride
ethylene bis(1-cyclopentadienyl) hafnium dimethyl
ethylene bis(1-cyclopentadienyl) hafnium diethoxide
ethylene bis(1-indenyl) hafnium dichloride
ethylene bis(1-indenyl) hafnium dimethyl
ethylene bis(1-indenyl) hafnium diethoxide
ethylene (1-indenyl)(1-cyclopentadienyl) hafnium dichloride
ethylene (1-indenyl)(1-cyclopentadienyl) hafnium dimethyl
ethylene (1-indenyl)(1-cyclopentadienyl) hafnium diethoxide
ethylene (1-indenyl)(9-fluorenyl) hafnium dichloride
ethylene (1-indenyl)(9-fluorenyl) hafnium dimethyl
ethylene (1-indenyl)(9-fluorenyl) hafnium diethoxide The double ligand according to the invention is a compound containing at least two cyclopentadiene groups, substituted or not, which are chemically interbonded. Examples of substituted cyclopentadiene groups are fluorene and indene groups.

Examples of double ligands according to the invention are:
dimethylsilyl bis(1-indene)
dimethylsilyl (9-fluorene)(1-cyclopentadiene)
dimethylsilyl bis(9-fluorene)
dimethylsilyl bis(1-cyclopentadiene)
dimethylsilyl bis(1-indene)
dimethylsilyl (1-indene)(1-cyclopentadiene)
dimethylsilyl (1-indene)(9-fluorene)
dimethylsilyl (9-fluorene)(1-cyclopentadiene)
2,2-propyl bis(1-indene)
2,2-propyl bis(trimethyl cyclopentadiene)
2,2-propyl bis(5-dimethylamino-1-indene)
2,2-propyl bis(6-dipropylamino-1-indene)
2,2-propyl bis(4,7-bis(dimethylamino-1-indene)
2,2-propyl bis(5-diphenylphosphino-1-indene)
2,2-propyl (1-dimethylamino-9-fluorene)(1-cyclopentadiene)
2,2-propyl (4-butylthio-9-fluorene)(1-cyclopentadiene)
2,2-propyl bis(4,5,6,7-tetrahydro-1-indene)
2,2-propyl bis(4-methyl-1-indene)
2,2-propyl bis(5-methyl-1-indene)
2,2-propyl bis(6-methyl-1-indene)
2,2-propyl bis(7-methyl-1-indene)
2,2-propyl bis(5-methoxy-1-indene)
2,2-propyl bis(4,7-dimethoxy-1-indene)
2,2-propyl bis(2,3-dimethyl-1-indene)
2,2-propyl bis(4,7-dimethyl-1-indene)
2,2-propyl (9-fluorene)(1-cyclopentadiene)
2,2-propyl bis(9-fluorene)
2,2-propyl bis(1-cyclopentadiene)
2,2-propyl bis(1-indene)
2,2-propyl (1-indene)(1-cyclopentadiene)
2,2-propyl (1-indene)(9-fluorene)
diphenylmethyl bis(1-indene)
diphenylmethyl (9-fluorene)(1-cyclopentadiene)
diphenylmethyl bis(9-fluorene)
diphenylmethyl bis(1-cyclopentadiene)
diphenylmethyl bis(1-indene)
diphenylmethyl (1-indene)(1-cyclopentadiene)
diphenylmethyl (1-indene)(9-fluorene)
diphenylsilyl bis(1-indene)
diphenylsilyl (9-fluorene)(1-cyclopentadiene)
diphenylsilyl bis(9-fluorene)
diphenylsylil bis(1-cyclopentadiene)
diphenylsilyl bis(1-indene)
diphenylsilyl (1-indene)(1-cyclopentadiene)
diphenylsilyl (1-indene)(9-fluorene)
ethylene bis(1-indene)
ethylene bis(trimethyl cyclopentadiene)
ethylene bis(5-dimethylamino-1-indene)
ethylene bis(6-dipropylamino-1-indene)
ethylene bis(4,7-bis(dimethylamino)-1-indene)
ethylene bis(5-diphenylphosphino-1-indene)
ethylene (1-dimethylamino-9-fluorene)(1-cyclopentadiene)
ethylene (4-butyl thio-9-fluorene)(1-cyclopentadiene)
ethylene bis(4,5,6,7-tetrahydro-1-indene)
ethylene bis(4-methyl-1-indene)
ethylene bis(5-methyl-1-indene)
ethylene bis(6-methyl-1-indene)
ethylene bis(7-methyl-1-indene)
ethylene bis(5-methoxy-1-indene)
ethylene bis(4,7-dimethoxy-1-indene)
ethylene bis(2,3-dimethyl-1-indene)
ethylene bis(4,7-dimethyl-1-indene)
ethylene (9-fluorene)(cyclopentadiene)
ethylene bis(9-fluorene)
ethylene bis(1-cyclopentadiene)
ethylene bis(1-indene)
ethylene (1-indene)(1-cyclopentadiene)
ethylene (1-indene)(9-fluorene)

The proton acceptor is a compound capable of reacting according to reaction (I) with two protons of the double ligand, yielding a bivalent anion hereinafter referred to as the double anion. If the double ligand contains cyclopentadiene, indene and/or fluorene groups, each of these groups may release one proton, yielding cyclopentadienyl, indenyl and fluorenyl anions.

Examples of suitable proton acceptors are: organometallic compounds, amines, metal hydrides and alkali or earth alkali metals. According to the invention it is preferred to use an alkali organometallic compound or an earth alkali organometallic compound as proton acceptor, particularly an alkyl lithium or an alkyl sodium compound, and use is made in particular of methyl or butyl lithium.

Reaction (I) may be a direct metalation reaction, for instance:

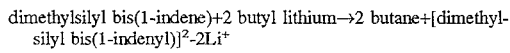

However, reaction (I) may also take the form of a redox reaction, an example being:

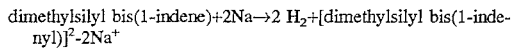

The reaction conditions for reaction (I) are not very critical, though substances that may react with the double ligand or the proton acceptor, such as water and oxygen, should virtually be absent. Therefore reaction (I) is usually carried out in a nitrogen atmosphere. The reaction pressure is immaterial. Usually a pressure of 0–0.2 MPa is used, more in particular atmospheric pressure. All pressures will here be given as absolute pressure. The temperature during reaction (I) is −100° to 100° C., preferably −80° to 50° C. A change in the temperature during the reaction does not have any harmful effects.

Reaction (I) is carried out in a known manner in a liquid dispersant. The double ligand concentration is higher than 0.001 mol/l, preferably 0.01–10 mol/l, in particular 0.05–5 mol/l. The proton acceptor concentration is higher than 0.001, preferably 0.01–10 mol/l, and in particular 0.05–10 mol/l. The advantage of the process according to the invention is that relatively high concentrations of double ligand and proton acceptor can be used.

The double anion formed as reaction product of reaction (I) is subsequently converted with a metal compound Me(Q)$_p$, Me being a metal ion of a group 4b, 5b or 6b metal from the Periodic System of Elements, while Q and p have the same meanings as in formula (2). This reaction proceeds according to the general reaction equation:

$$C_2^{2+}+L-L^{2-}+Me(Q)_p \rightarrow L-L-MeQ_{p-2}+2CQ \quad (II)$$

where C is a cation and L—L the double ligand. An example is:

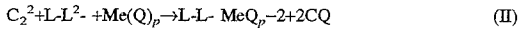

According to the invention reaction (II) is carried out in a liquid dispersant comprising one or more weak Lewis bases, the conjugated acid of which has a dissociation constant $pK_a$ ≦−2.5 and contains at most 1 mole equivalent, relative to the metal compound, of strong Lewis base, the conjugated acid of which has a $pK_a$ higher than −2.5. The $pK_a$ values cited here are based on D. D. Perrin: Dissociation Constants of Organic Bases in Aqueous Solution, International Union of Pure and Applied Chemistry, Butterworths, London 1965. The values were determined in an aqueous $H_2SO_4$ solution.

Reaction (II) is preferably carried out under such reaction conditions that the double anion and the Me(Q)$_p$ metal compound form a suspension in the liquid dispersant.

The liquid dispersant preferably comprises one or more weak Lewis bases, the conjugated acid of which has a $pK_a$ of between −2.5 and −15, a value between −2.5 and −10 having greater preference. The ethers are examples of suitable dispersants according to the invention. Particularly suitable dispersants are dimethoxy ethane ($pK_a$=−2.97), ethoxy ethane ($pK_a$=3.59), isopropoxy isopropane ($pK_a$=−4.30), methoxy methane ($pK_a$=−3.83), n-propoxy-propane ($pK_a$=−4.40), n-butoxy-n-butane ($pK_a$=−5.40), ethoxy-n-butane ($pK_a$=−4.12), methoxy benzene ($pK_a$=−6.54), dioxane ($pK_a$=−2.92). Also highly suitable are dispersants consisting of 100–10 vol. % weak Lewis bases and 0–90 vol. % aliphatic hydrocarbon, preferably 100–50 vol. % weak Lewis bases and 0–50 vol. % aliphatic hydrocarbon.

According to the invention it is possible to accurately control the stereoconfiguration of the bridged dicyclopentadienyl-compounds, by altering the Lewis base used as a liquid dispersant in reaction (II). The effect of the alteration of strength of the Lewis base is shown in the examples.

The molecules of the compounds can have two optical active centres and the compounds therefore can occur in two different stereoconfigurations designated as racemic-form (rac.) and meso-form. The presence of the racemic form and the meso form and the ratio rac./meso can be determined using H-NMR in a way known as such.

In the preparation of polypropylene the racemic form leads to the production of isotactic polypropylene, whereas the meso-form leads to the production of atactic polypropylene, which is an undesirable product. It is therefore advantageous to produce only the racemic form of the metallocene compounds. This is possible according to the invention. In case that both the rac.- and meso-form are formed a high value of the ratio rac./meso possible, which is also advantageous for use in the preparation of polypropylene.

In polymerisation processes for the preparation of ethylenepolymers or ethylene-propylene-diene-monomer rubbers both the racemic and the meso-form can yield suitable products. High relative amounts of either the racemic or the meso form can be advantageous, e.g. in the preparation of ethylene-propylene-diene-monomer rubbers, because the racemic and the meso-form yield different types of rubber. Also the catalytic activity of the rac. and meso-form can be different which can lead to a preference for either the rac.- or the meso-form.

The metal compound Me(Q)$_p$ is preferably a zirconium, titanium or hafnium compound. There is advantage in choosing the metal compound from compounds of the formula MeQ$_4$, Me standing for zirconium, titanium or hafnium, with a formal oxidation state of 4, and Q being the same or different groups, chosen from alkyl-, aryl-, aryl alkyl-, alkyl aryl-, amide-, alkoxy-, halogenide-, sulphide-, hydride-or phosphorus-containing groups. More preferably, Q are the same or the different alkoxy or halogenide groups. The metal compound according to the invention is in particular zirconium tetrachloride, hafnium tetrachloride, tetrabutoxy zirconium or zirconium dibutoxy dichloride.

The reaction product of reaction (II) may contain the metallocene compound in the form of a complex or mixture with salts and/or with the Lewis bases. An example is [dimethylsilyl bis(1-indenyl)]ZrCl$_2$.2 LiCl.0.5 $CH_3CH_2OCH_2CH_3$. For use as a catalyst component for the polymerization of olefins such complexes usually need to be converted into non-complexed metallocene compounds or be isolated from the mixture. Surprisingly, the bridged metallocene compounds according to the invention exhibit a high activity also in complexed or mixed form. This makes it possible to use the reaction product of reaction (II) directly as catalyst component, without removal of the complexed compounds or separation of the mixtures being necessary. Should such removal or separation be desired, then this can be effected in a known manner, for instance extraction with a solvent that is suitable for the metallocene compounds but not for the compounds to be removed. An example of such a solvent is dichloro methane.

The bridged metallocene compounds according to the invention can be used according to methods known per se as a catalyst component for the polymerization of olefins. They are known, for instance, as catalyst component for the production of polyethylene, polypropylene and ethylene-propylene-(third monomer)-rubbers or EP(D)M rubbers. In that case the catalyst component may be mounted on an inert support such as silica.

The metallocene compounds are used in a known way in combination with a cocatalyst, usually an aluminium compound. Cocatalysts based on aluminium compounds, for instance, can be found in EP-A-0287666, pages 20–21. Other suitable cocatalysts are benzene-insoluble organo-aluminium compounds, as known from EP-A-0360492. See also US-A-4769428 (column 5), where organoaluminium alkyls and linear and cyclic alumoxanes are used as cocatalysts. The alumoxanes can be prepared in the ways disclosed in said patent publications, but they are commercially available. Examples of commercial alumoxanes are methyl alumoxanes from Schering and Texas Alkyls.

As solid or as suspension in an inert solvent the bridged metallocene compounds according to the invention have a very high stability, so that they can be stored for a long time. This contrasts with the known bridged metallocene compounds, which are sensitive to degradation, leading to a decrease in the polymerization activity. The invention therefore provides a catalyst component that is suitable for the polymerization of olefins, comprising a bridged metallocene compound prepared by the process according to the invention, characterized in that the catalyst component comprises a suspension of the metallocene compound in an inert solvent.

Polymerization can be effected in a known manner, taking place in the gas phase or in a liquid reaction medium. An inert solvent or the olefin can be used as reaction medium. The polymerization may be solution polymerization, suspension polymerization, bulk polymerization or gas phase polymerization. It can be carried out either continuously or discontinuously, at high pressures, from 50–300 MPa, as well as low pressures, from 0.1–50 MPa.

The invention also relates to a process for the preparation of olefins.

The polymerization of olefins is preferably effected in a liquid polymerization medium which contains at least an olefin, this liquid polymerization medium comprising aliphatic hydrocarbon and the bridged metallocene compound forming a suspension in the polymerization medium. In such a preferred embodiment the bridged metallocene compounds according to the invention have a sufficiently high activity, in contrast to the known bridged metallocene compounds. In particular, the catalyst component can also be used as a suspension of the metallocene compound in an inert dispersant. The advantage of the embodiment is that use can be made of dispersants customarily used in industrial-scale polymerization of olefins, such as gasoline. This is advantageous since these dispersants are cheaper and safer than aromatic hydrocarbons, which until now were needed in the polymerization with bridged metallocene catalysts.

The invention is further aimed at a polyolefin that can be obtained by the process for the polymerization of olefins according to the invention.

The invention will be elucidated on the basis of the following examples and comparative experiments, which are non-restrictive; the examples have, for instance, not been optimized with respect to the amount of dispersant, reaction temperature, etc. Metallocene compounds synthesized in the experiments were analyzed by means of neutron activation analysis and H—NMR (hydrogen—nuclear magnetic resonance). With neutron activation analysis the concentrations of elements can be determined in a known way. H—NMR supplies information on the structure of the metallocene compounds. The resonance peaks of the racemic- and meso-form of many metallocene compounds are given in the literature. The H—NMR analyses were performed in a known manner using a Bruker AC200 NMR apparatus at a frequency of 200 MHz. The samples for NMR analysis were prepared by adding c. 1 ml of deuterobenzene to 1–10 mg of metallocene compound.

EXAMPLE I

Synthesis of [isopropyl(9-fluorenyl)(1-cyclopentadienyl) zirconium dichloride 13.41 ml of a 1.74M solution in hexane of butyl lithium was added to a cooled solution (−56° C.) of 3.18 g (11.67 mmol) of isopropyl (9-fluorene)(1-cyclopentadiene) in 40 ml of diethyl ether in a Schlenk flask. During heating to 25° C. the solution changed from bright yellow via orange/red into an orange/yellow suspension. After cooling to −56° C. the suspension was added to a suspension of 2.72 g of zirconium tetrachloride in 40 ml of diethyl ether, which had been cooled to −56° C. Immediately upon the addition the cooling medium was removed. After two minutes already an orange/red suspension had been obtained. After the reaction temperature had reached room temperature (after two hours), the solid matter was filtered off and washed one time with 30 ml of diethyl ether; the wash liquid had a bright red colour.

Yield after vacuum drying: 5.86 g of red solid (85% yield on Zr basis) consisting of [isopropyl(9-fluorenyl)(1cyclopentadienyl) zirconium dichloride] complexed or mixed with 2 mole equivalents of lithium chloride and 1 mole equivalent of diethyl ether per mole of metallocene compound. The product thus obtained is air stable for at least 72 hours.

EXAMPLE II

A. Synthesis of dimethylsilyl bis(1-indene) (reaction I))

9.89 ml of a 1.74M solution in hexane of butyl lithium was added to a solution cooled to −56° C. of 2.01 g (17.2 mmol) of indene in 40 ml of diethyl ether. Subsequently, 1.11 g (8.6 mmol) of dimethylsilyl dichloride was added to the solution. After stirring for one hour the precipitate formed (lithium chloride) was filtered off.

B. Synthesis of [dimethylsilyl bis(1-indenyl) zirconium dichloride]

The solution obtained under A was cooled to −56° C., after which 9.9 ml of a 1.74M solution in hexane of butyl lithium was added. The reaction was further carried out as in Example 1, but now with 2 g of ZrCl$_4$ (8.6 mmol). The product of the reaction was an orange powder (3.14 g; 64% yield), which upon analysis proved to be (rac.)dimethylsilyl bis(1-indenyl) zirconium dichloride, complexed or mixed with 2 mole equivalents of lithium chloride and 0.5 mole equivalent of diethyl ether per mole of metallocene compound. This product is air stable.

EXAMPLE III

Synthesis of [diphenyl (9-fluorenyl)(1-cyclopentadienyl) zirconium dichloride]

Synthesis as in Example I, now with:

1.38 g of diphenyl (9-fluorene)(1-cyclopentadiene)(3.48 mmol)

4.35 ml of 1.6M butyl lithium (6.96 mmol)

0.81 g of zirconium tetrachloride (3.48 mmol)

The dark red [diphenyl (9-fluorenyl) (1-cyclopentadienyl) zirconium dichloride compound was obtained in a yield of 75% and is air stable.

COMPARATIVE EXPERIMENT A

Synthesis of [isopropyl (9-fluorenyl)(1-cyclopentadienyl) zirconium dichloride]

This compound was synthesized on the basis of zirconium tetrachloride complexed with 2 mole equivalents of tetrahydrofuran (THF) per mole of zirconium tetrachloride
Synthesis as in Example I, now with:

2.17 g of isopropyl (9-fluorene) (1-cyclopentadiene) (7.95 mmol)

9.94 ml of 1.6M butyl lithium (15.9 mmol)

3.00 g of $ZrCl_4 \cdot 2THF$ (7.95 mmol). A brown suspension was obtained. The solid obtained after upgrading, in a yield of 3.37 g, is an impure orange/brown product which decomposes in the air.

EXAMPLE IV

Polymerization of ethylene

The reaction product of Example I was used for solution polymerization of ethylene. At an inlet temperature of 155° C. and a pressure of 20 bar, 1 ml of a suspension of 0.44 g of the reaction product in 50 ml of gasoline (0.015M zirconium), 10 ml of a 1.6M methyl alumoxane (MAO) solution in toluene and 50 ml pentamethylheptane was metered to a 1.1 l reactor filled with 450 ml of heptane. The methyl alumoxane, type TA-01629, was supplied by Schering'; its aluminium content was 5 wt. % and its molecular weight 1100 g/mol. Polymerization started immediately, causing a 34° C. jump in the temperature, which was indicative of a high polymerization activity. After 10 minutes the polyethylene (PE) solution was drained and upgraded. Yield: 23 g of PE.

EXAMPLE V

Polymerization of ethylene

Example IV was repeated, but now 8 ml of the MAO solution was used. Yield: 19.5 g of PE.

EXAMPLE VI

Polymerization of propylene

The reaction product of Example I, metered as a suspension in gasoline and with MAO (as in Example IV) as cocatalyst, was used for the suspension polymerization of propylene. For 25 minutes propylene was polymerized at a temperature of 40° C. and a pressure of 6 bar in a 1.3 l reactor filled with 500 ml of heptane. The zirconium concentration was $9.3 \times 10^{-3}$ mM, and the Al concentration 58.5 mM. After draining and upgrading 32 g of polypropylene was obtained, its DSC melting point being 138° C.

EXAMPLE VII

Polymerization of propylene

Example VI was repeated, the MAO concentration (calculated for aluminium) now being 10.3 mM. Yield: 17 g of polypropylene with a DSC melting point of 143° C.

EXAMPLE VIII

Polymerization of ethylene and propylene

The reaction product of Example I was used for the solution copolymerization of ethylene and propylene. At an inlet temperature of 30° C. and a pressure of 7 bar, 2 mg of the reaction product in 100 ml of gasoline (suspension) and 1.75 ml of a MAO solution in toluene were metered to a 1.0 l reactor filled with 400 ml of gasoline. The MAO solution contained an amount of MAO equal to 30 wt. % of aluminium. The ethylene and propylene flow rates amounted to 75 and 150 l/hr, respectively. During 60 minutes of polymerization a temperature jump of 21° C. was reached. After draining and upgrading 143 g of ethylene propylene (EP) rubber was isolated.

COMPARATIVE EXPERIMENT B

Polymerization of ethylene and propylene

Example VIII was repeated, but now with [isopropyl(9-fluorenyl(1-cyclopentadienyl) zirconium dichloride, prepared according to method B on page 6 of EP-A-0351392. The temperature jump was only 5.5° C., and the yield 49 g of EP rubber.

EXAMPLE IX

Synthesis of (1,2-ethylene(bis-(1-indenyl) zirconium-dichloride)

Synthesis as in Example I now with:

9.19 g (1,2-ethylene(bis-(1-indene)) (35.58 mmole) in 40 ml diethylether, 44.48 ml butyllithium 1.6M in hexane (71.16 mmole).

8.29 g $ZrCl_4$ (35.58 mmole) in 40 ml diethylether
Yield of stable orange/yellow substance>95%. The ratio rac/meso is 55/45 determined by H-NMR.

EXAMPLE X

Synthesis of (1,2-ethylene(bis-(1-indenyl) zirconium-dichloride)

Synthesis of the dianion of (1,2-ethylene-(bis-(1-undenyl) zirconiumdichloride) was carried out as in Example I using:

6.75 g (1,2-ethylene(bis-(1-indene))) (26.13 mmole) in 120 ml diethylether 32.66 ml butyllithium 1.6M hexane (52.55 mmole).

The formed precipitate (dianion) was filtered off and washed with 120 ml gasoline (hexane), suspended in 80 ml dimethoxyethane, cooled to −20° C.

A solution having a temperature of −56° C. of 5.78 g $ZrCl_4$ (24.80 mmole) was added.

The reaction mixture was a green suspension the colour of which changed through brown into yellow (after 24 h). The yellow precipitate was filtered off and dried. Yield: 65% air stable rac-(1,2-ethylene(bis-(1-indenyl)-zirconiumdichloride.

EXAMPLE XI

Synthesis of (1,2-ethylene(bis-(1-indenyl) zirconium-dichloride)

A Synthesis was conducted as in Example X using 2.86 g dianion (11.07 mmole) slurried in 40 ml anisole 13.84 ml butyllithium 1.6M in hexane (22.14 mmole) 2.20 g ZrCl$_4$ (9.44 mmole) in 40 ml anisole. The formed precipitate was filtered off.
Yield: 80% air stable 1:1 rac/meso (1,2-ethylene(bis-(1-indenyl)zirconiumdichloride
The filtrate was not used.

I claim:
1. A process for preparing a bridged metallocene compound having the formula:

wherein
CpR$_n$ is a cyclopentadienyl or indenyl group, whether or not substituted with one or more alkyl, phosphine, amine, alkyl ether, thio, or aryl ether groups;
CpR'$_m$ is a cyclopentadienyl or indenyl group, whether or not substituted with one or more alkyl, phosphine, amine, alkyl ether, thio or aryl ether groups;
R" is a structural bridge between the Cp rings;
Me is a metal from Group 4b of the Periodic System of Elements;
each Q is independently selected from the group consisting of alkyl-, aryl-, arylalkyl-, alkylaryl-, amide-, alkoxy-, halogenide-, sulphide-, hydride- and phosphorous-containing groups, and
m, n and p are integers, wherein $0 \leq n \leq 4$, $0 \leq m \leq 4$, and $1 \leq p \leq 4$ which comprises,
 (a) allowing a bridged double ligand having at least two chemically interbonded cyclopentadiene groups to react with a proton acceptor which is capable of reacting with said bridged double ligand whereby a bridged double anion is obtained,
 (b) converting said bridged double anion into said bridged metallocene compound by allowing said bridged double anion to react with a metal compound wherein the metal component thereof is selected from the group consisting of metals from Group 4b of the Periodic System of Elements, in a liquid dispersant which comprises at least one weak Lewis base, the conjugated acid of which has a dissociation constant pKa wherein the pKa is $\leq -2.5$,
 wherein the liquid dispersant contains from 0 to at most 1 mole equivalent, relative to the metal compound, of a strong Lewis base, the conjugated acid of which has a pKa which is greater than $-2.5$.
2. The process according to claim 1, where said bridged double ligand is selected from the group consisting of
dimethylsilyl bis(1-indene),
dimethylsilyl bis(1-cyclopentadiene),
dimethylsilyl bis(1-indene),
dimethylsilyl (1-indene)(1-cyclopentadiene),
2,2-propyl bis(1-indene),
2,2-propyl bis(trimethyl cyclopentadiene),
2,2-propyl bis(5-dimethylamino-1-indene),
2,2-propyl bis(6-dipropylamino-1-indene),
2,2-propyl bis(4,7-bis(dimethylamino)-1-indene),
2,2-propyl bis(5-diphenylphosphino-1-indene),
2,2-propyl his(4,5,6,7-tetrahydro-1-indene),
2,2-propyl bis(4-methyl-1-indene),
2,2-propyl bis(5-methyl-1-indene),
2,2-propyl bis(6-methyl-1-indene),
2,2-propyl bis(7-methyl-1-indene),
2,2-propyl bis(5-methoxy-1-indene),
2,2-propyl bis(4,7-dimethoxy-1-indene),
2,2-propyl bis(2,3-dimethyl-1-indene),
2,2-propyl bis(4,7-dimethyl-1-indene),
2,2-propyl bis(1-cyclopentadiene),
2,2-propyl bis(1-indene),
2,2-propyl (1-indene)(1-cyclopentadiene),
diphenylmethyl bis(1-indene),
diphenylmethyl bis(1-cyclopentadiene),
diphenylmethyl bis(1-indene),
diphenylmethyl (1-indene)(1-cyclopentadiene),
diphenylsilyl bis(1-indene),
diphenylsilyl bis(1-cyclopentadiene),
diphenylsilyl (1-indene)(1-cyclopentadiene),
ethylene bis(1-indene),
ethylene (trimethyl cyclopentadiene),
ethylene (5-dimethylamino-1-indene),
ethylene bis(6-dipropylamino-1-indene),
ethylene bis(4,7-bis(dimethylamino)-1-indene),
ethylene bis(5-diphenylphosphino-1-indene),
ethylene bis(4,5,6,7-tetrahydro-1-indene),
ethylene bis(4-methyl-1-indene),
ethylene bis(5-methyl-1-indene),
ethylene bis(6-methyl-1-indene),
ethylene bis(7-methyl-1-indene),
ethylene bis(5-methoxy-1-indene),
ethylene bis(4, 7-dimethoxy-1-indene),
ethylene bis(2,3-dimethyl-1-indene),
ethylene bis(4,7-dimethyl-1-indene),
ethylene bis(1-cyclopentadiene),
ethylene bis(1-indene),
ethylene (1-indene)(1-cyclopentadiene), and.
3. A process according to claim 1, wherein (b) is carried out under such reaction conditions that the bridged double anion and the compound of a Group 4b metal of the Periodic System of Elements form a suspension in the liquid dispersant.
4. A process according to claim 1, wherein the liquid dispersant comprises at least one weak Lewis base, the conjugated acid of which has a pKa between $-2.5$ and $-15$.
5. A process according to claim 4, wherein the liquid dispersant comprises one or more weak Lewis bases, the conjugated acid of which has a pK$_a$ between $-2.5$ and $-10$.
6. A process according to claim 5, wherein the liquid dispersant comprises one or more ethers.
7. A process according to claim 6, wherein the liquid dispersant is at least one member selected from the group consisting of dimethoxy ethane, ethoxy ethane, n-butoxy-n-butane, isoproxy isopropane, methoxy methane, n-propoxy-n-propane, ethoxy-n-butane, methoxy benzene, and dioxane.

8. A process according to claim 1, wherein the metal compound is a zirconium, titanium or hafnium compound.

9. A process according to claim 8, wherein the metal compound is selected from the group consisting of compounds having the formula $$MeQ_4$$

wherein Me is zirconium, titanium or hafnium, with a formal oxidation state of 4; and each Q is the same or different, and is selected from the group consisting of alkyl-, aryl-, aryl alkyl-, alkyl aryl-, amide-, alkoxy-, halogenide-, sulphide-, hydride-, and phosphorus-containing groups.

10. A process according to claim 9, wherein Q are the same or different alkoxy or halogenide groups.

11. A process according to claim 10, wherein the metal compound is zirconium tetrachloride, hafnium tetrachloride, tetrabutoxy zirconium or zirconium dibutoxy dichloride.

12. A process according to claim 1, wherein the metal compound is a titanium compound.

13. A process according to claim 1, wherein the metal compound is a hafnium compound.

14. A process according to claim 1, wherein said liquid dispersant is at least one weak Lewis base.

15. A process for preparing a bridged metallocene compound having the formula:

$$R''(CpR_n)(CpR'_m)Me(Q)_p$$

wherein

CpR$_n$ is a cyclopentadienyl or indenyl group, whether or not substituted with one or more alkyl, phosphine, amine, alkyl ether, thio or aryl ether groups;

CpR'$_m$ is a cyclopentadienyl or indenyl group, whether or not substituted with one or more alkyl, phosphine, amine, alkyl ether, thio or aryl ether groups;

R'' is a structural bridge between the Cp rings;

Me is a metal from Group 4b from the Periodic System of Elements;

each Q is independently selected from the group consisting of alkyl-, aryl-, arylalkyl-, alkylaryl-, amide-, alkoxy-, halogenide-, sulphide-, hydride-and phosphorous-containing groups, and m, n and p are integers, wherein $0 \leq n \leq 4$, $1 \leq m \leq 4$, and $1 \leq p \leq 4$ which comprises, (a) allowing a bridged double ligand having at least two chemically interbonded cyclopentadiene groups to react with a proton acceptor which is capable of reacting with said bridged double ligand whereby a bridged double anion is obtained, (b) converting said bridged double anion into said bridged metallocene compound by allowing said bridged double anion to react with a metal compound in a liquid dispersant wherein the metal component thereof is selected from the group consisting of metals from Group 4b of the Periodic System of Elements, wherein the liquid dispersant consists of 100–50 vol. % of at least one weak Lewis base and 0–50 vol. % of aliphatic hydrocarbon, and wherein the conjugated acid of the at least one weak Lewis base has a dissociation constant pKa which is $\leq -2.5$.

* * * * *